June 25, 1974 F. J. CAMPBELL Plant Pat. 3,578
RED CHIEF
Filed Aug. 24, 1972
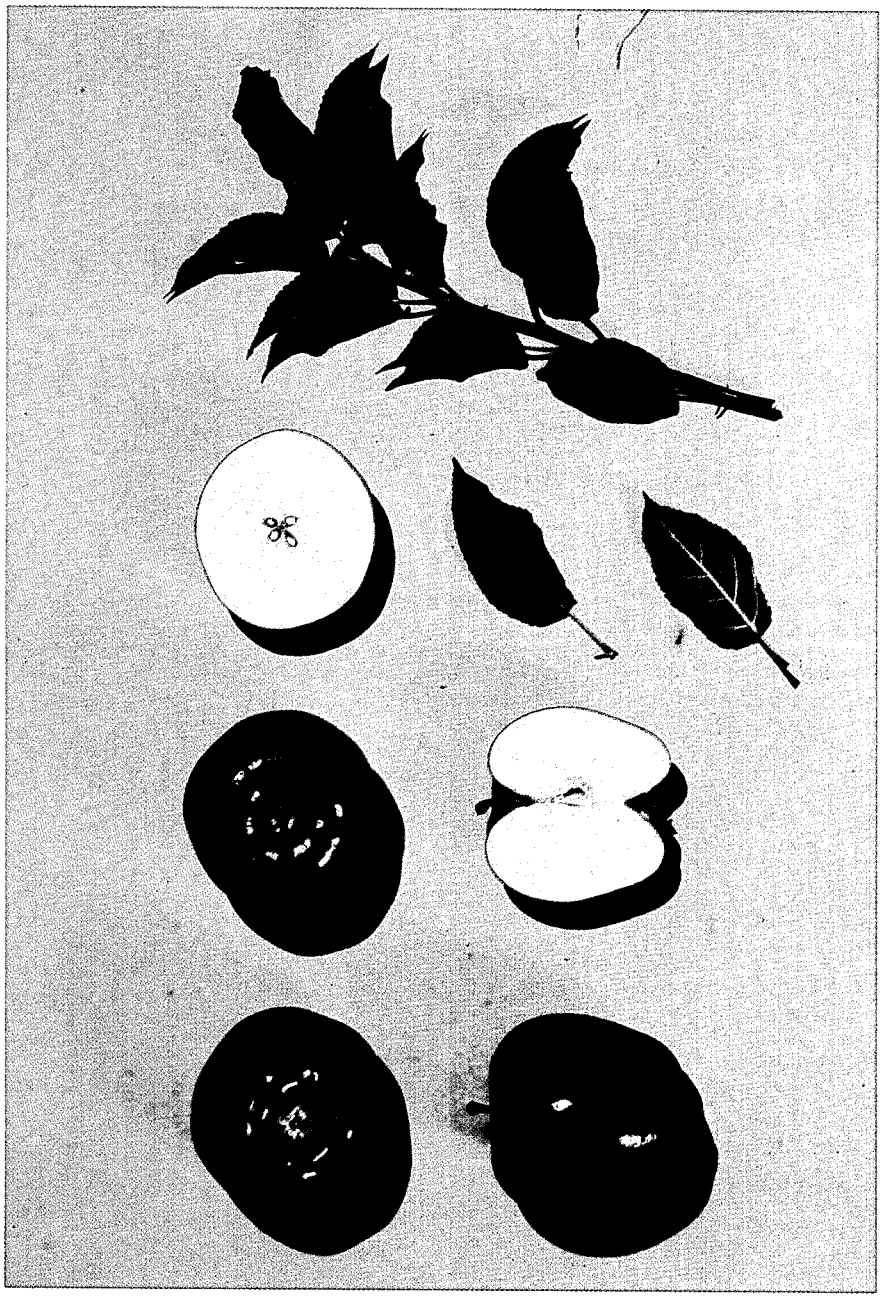

United States Patent Office

Plant Pat. 3,578

Patented June 25, 1974

3,578
APPLE TREE

Fred J. Campbell, Othello, Wash., assignor to Hilltop Orchards & Nurseries, Inc.

Filed Aug. 24, 1972, Ser. No. 283,500
Int. Cl. A01h 5/03
U.S. Cl. Plt.—35 1 Claim This invention is a new and distinct cultivar of apple tree discovered by Fred J. Campbell in June 1967 as a limb mutation on a Bisbee strain "Delicious" apple tree. It originated in an orchard located in Farm Unit No. 109, Range No. 69, Block No. 87, Columbia Basin Project, Grant County, Wash. The farm is and was owned by Fred J. Campbell, who is the originator and discoverer of the cultivar.

The mutated limb was propagated by bud grafting into 93 young trees near the original tree. The unique characteristics of the sported limb have been maintained through asexual propagation.

Fruit of the new cultivar, which we have since named "Red Chief" has been observed since 1967 on the original limb in 1970 and 1971 and from trees budded in 1968. The following description is based on fruit from both the original and asexually propagated trees.

TREE

Form: The tree is small and vigorous with an upright and vase-shaped form. It bears regularly and is productive. The tree appears to be as hardy as "Delicious." The branches have a profusion of fruit spurs with shorter than normal internodes. I classify "Red Chief" as spur type and semi-dwarf. The trunk of the tree is stocky and smooth; the branches, rather thick and smooth with a reddish-brown to gray color. The lenticels on the wood are few, medium in size, and raised.

Leaf: Leaves are medium in length and width, dark green, and thick. They are abruptly pointed and rugose with finely serrate margins. The petiole is medium in length and thickness. There is a red stripe on the underside of the petiole, especially intense at the base which extends up the midrib of the leaf.

Flowers: In Washington State the average first opening date is April 28 and the average date of full bloom is May 1 as in "Delicious" (Bisbee strain). Flowers are medium in size and white.

FRUIT

Shape: The fruit shape of "Red Chief" resembles "Delicious" but is more pronounced and distinct. Because of its long and drawn-out shape with prominent calyx lobes, the fruit shape is considered "very typey." The form is very uniform with a slight tendency to ribbing to the five prominent points on the calyx. The basin end is very symmetrical, fairly narrow and rounded, with high shoulders. The average transverse diameter of the fruit is 3 inches, and the axial-diameter is 3¼ inches. The calyx is open and the segments are very persistent with both inner and outer surfaces pubescent. The eye is medium in size and partially open. The stamens occur as one distinct whorl.

Skin: Fruit skin is thick, tough, smooth, and glossy. The conspicuous lenticels are small, circular, and slightly depressed and occur relatively infrequently on the shoulder but more frequently toward the calyx. Their color is white to creamy white. The fruit skin is more resistant to sunburn (buckskinning) than Bisbee strain "Delicious" at temperatures up to 100° F.

Skin Color: Ground color is an attractive yellow with over-color which initiates very early as a prominent stripe from the stem to the calyx. This occurs at least four (4) weeks previous to color development on any known color sports or strains of "Delicious." The stripping gradually fills in with a bright red over-color and covers the stripes. At maturity the apple fruit is a very bright red color with a faint hint of an under-stripe showing through. The color as identified with the Nickerson Color Fan from the Munsell Color Company from the darkest stripping is Dark Red, 5R 3/7 with lighter red colors ranging from Strong Red, 5R 4/12 to near Vivid Red, 5R 5/13.

Flesh: The flesh is very juicy, firm and crisp, and white to creamy-white, tinged with red in the cortex near the skin vascular bundles and calyx tube. The core is symmetrical and fairly large. The bundles are conspicuous and yellowish in color with the core lines distinct and clasping. The calyx tube is pubescent and the stem of the funnel is rather long. The seed cells are open and distant and quite tough with an average length of ¾ inch. The flavor is mild and sweet and rather rich. The aroma is pronounced and good.

Seeds: The seeds are perfect and a full complement of 10 usually develops. The seeds are about 5/16 inch long and 3/16 inch wide; the color is a distinct brown.

Pedicel: The pedicel is medium thick, pubescent with an average length of 1 inch. The pedicel color is prominently red-striped which develops early in the growing season coinciding with the stripping on the apple skin. The red stripes run the full length of the stem and flare out into the basin, appearing about a month after bloom on until maturity. This red striping of the pedicel is one of the distinguishing characteristics of "Red Chief."

Maturity: The fruit matures at least a week before Bisbee strain "Delicious" based on visual disappearance of green flesh color and starchiness in taste. Early fruit maturity is one of the promising characteristics of "Red Chief."

Use: The fruit is all-purpose but particularly adaptable for fresh use as a dessert apple. It is an excellent keeper with 150 days average storage life under normal refrigerated storage conditions.

The outstanding features of "Red Chief" which make it unique and valuable are as follows:

(1) A combination of spur type growth habit and an early developing striped red color pattern earlier than any other "Delicious" strain.
(2) A striped pattern that blends into a solid bright red color ahead of actual fruit maturity.
(3) A distinctly stronger color factor than any "Delicious" strain in reference to depth, brightness and earliness of color development.
(4) A yellow under-color with little tendency for green or olive-colored undercolor.
(5) A white to creamy-white flesh with little tendency to produce a greenish color.
(6) A very long and drawn out shape with very prominent calyx lobes which produces a "very typey" characteristic "Delicious" shape as grown in Washington State.
(7) Resistance of the fruit to sunburning in comparison with many other "Delicious" strains.
(8) A distinctive red stripe on the pedicel which helps identify "Red Chief."
(9) While the instant variety is somewhat similar to "Earlistripe," Plant Pat. No. 2,606. "Red Chief" shows extremely prominent striping when "Earlistripe" shows only a faint striping, when observed approximately a month prior to maturity. Further, the fruit of "Earlistripe" is definitely more conical. "Earlistripe" matures with more pronounced striping than all other striped spur strains known to the discoverer.

In summary.—The "Red Chief" apple has a new and unique combination of desirable characteristics including early developing, red-striped color pattern which matures into a solid, attractive, bright-red-colored skin, a "very typey" fruit shape, and a spur type growth habit that is semidwarf in character.

I claim:

1. A new and distinct variety of apple tree substantially as shown and described.

References Cited

UNITED STATES PATENTS

P.P. 2,606 3/1966 Cooper ---------- Plants—35

ROBERT E. BAGWILL, Primary Examiner